United States Patent [19]

Lerner et al.

[11] 4,340,458
[45] Jul. 20, 1982

[54] GLUCOSE SENSOR

[75] Inventors: Harry Lerner, Lexington; José D. Giner, Brookline; John S. Soeldner, Newton, all of Mass.

[73] Assignee: Joslin Diabetes Center, Inc., Boston, Mass.

[21] Appl. No.: 155,198

[22] Filed: Jun. 2, 1980

[51] Int. Cl.$^3$ ............... G01N 27/46; G01N 27/50
[52] U.S. Cl. ................. 204/195 R; 128/635; 204/1 T; 204/195 B
[58] Field of Search ........... 204/195 R, 195 B, 195 C, 204/1 T; 128/635

[56] References Cited

U.S. PATENT DOCUMENTS

| | | | |
|---|---|---|---|
| 3,282,804 | 11/1966 | Stearn | 204/195 R X |
| 3,428,532 | 2/1969 | Banks | 204/195 R X |
| 3,542,662 | 11/1970 | Hicks et al. | 204/195 |
| 3,623,960 | 11/1971 | Williams | 204/1 T |
| 3,837,339 | 9/1974 | Aisenberg et al. | 128/213 |
| 3,855,101 | 12/1974 | Wilson | 204/195 R |
| 3,922,205 | 11/1975 | McLean et al. | 204/1 T |
| 4,132,605 | 1/1979 | Tench et al. | 204/1 T |
| 4,140,963 | 2/1979 | Rao et al. | 324/30 R |

FOREIGN PATENT DOCUMENTS 1422172  1/1976  United Kingdom.
2019580 10/1979  United Kingdom.

OTHER PUBLICATIONS

Harry Lerner et al., J. Electrochem. Soc., vol. 126, No. 2, pp. 237-242, (1979).
Ljiljana Marincic et al., J. Electrochem. Soc., vol. 126, No. 10, pp. 1687-1692, (1979).
J. R. Rao et al., Biomat., Med. Dev. Art. Org., 6(2), 127-149, (1978).
Kuo Wei Chang et al., Trans. Amer. Soc. Artif. Int. Organs, vol. XIX, pp. 352-360, (1973).
U. Gebhardt et al., Bioelectrochemistry & Bioenergetics, 5, 607-624, (1978).
D. A. Gough et al., "Blood Glucose Monitoring", pp. 10-22, Georg Thieme Publishers, (1977).
Clark K. Colton, Transplantation & Clinical Immunology, vol. X, pp. 165-174, (1978).
Ljiljana Marincic et al., J. Electrochem. Soc., vol. 26, No. 1, pp. 43-49, (1979).
John R. Guyton et al., The Development of an Implantable Electrochemical Sensor, (1980).
J. S. Soeldner et al., In Vitro Studies of a Potentially Implantable Electrochemical Glucose Sensor, (1979).

*Primary Examiner*—G. L. Kaplan

[57] ABSTRACT

Glucose sensing apparatus for use in biological fluids comprising an electrode and a voltage source connected to the electrode to cause a current to flow therethrough, in which the voltage applied to the electrode is varied in a sweep ranging from a first limit to a second limit and back toward the first limit, and the current at the electrode is integrated with respect to time during at least a portion of the voltage variation selected to produce a total charge sensitive to glucose concentration and relatively insensitive to other components in the fluid; alternatively the current is measured at a point in a specific region of the voltage variation.

16 Claims, 13 Drawing Figures

GLUCOSE SENSOR CURRENT-TIME RESPONSE IN K/R BUFFER SOLUTION(1) AND POTENTIAL VS. TIME(2) FOR ONE COMPLETE POTENTIAL CYCLE

GLUCOSE SENSOR

BACKGROUND OF THE INVENTION

This invention relates to sensing the concentration of glucose in biological fluids.

It is desirable to monitor accurately glucose concentration in biological fluids, particularly using a device that is implantable in living organisms; for example, such a device would be useful for diabetics in timing the administration of insulin and food.

Glucose concentration in simple solutions—e.g., Krebs-Ringer buffer—can be monitored electrochemically by measuring the current density at a platinum electrode while varying the electrode potential relative to a standard. At various electrode potentials, current generated by electrochemical reactions is responsive to the glucose concentration. Accordingly, current measured while varying the electrode potential over a range, first from negative to positive (anodic) and then back again (cathodic), will be a function of glucose concentration.*

*Marincic et al., "Electrochemical Glucose Oxidation on a Platinized Platinum Electrode in Krebs-Ringer Solution, I. Potentiodynamic Studies", 126 J. Electrochem. Soc. 43, January 1979 and "III. Effect of Urea", 126 J. Electrochem. Soc. October 1979.

Interference with glucose measurement due to the presence of other biological substances—particularly amino acids and urea—is a serious problem. Such substances undergo electrochemical reactions during the voltage sweep, generating currents independent of glucose concentration and reducing sensitivity to glucose.

Marincic et al., supra, indicates that there is considerable sensitivity of current density to glucose concentration in the presence of urea with cathodic potential sweeps at potentials below about −100 mV; that article concludes, however, for anodic potential sweeps, that inhibition by urea precludes glucose concentration measurement.

Gebhart et al., "Development of an Implantable Electrocatalytic Glucose Sensor", 5 Bioelectrochemistry and Bioenergetics 607 (1978) indicates (FIG. 9) a correlation between glucose concentration in the presence of amino acids and charge produced at the electrode at a specific voltage; between periods of integration, voltage is shifted to a rejuvenation potential.

SUMMARY OF THE INVENTION

According to one aspect of the invention, by applying a voltage to the electrode, varying the voltage in a sweep from a limit first limit to a second limit and back toward the first limit, and integrating the current at the electrode over at least a portion of the voltage sweep selected to produce a total charge sensitive to glucose concentration and to be relatively insensitive to other components in the biological fluid, an accurate measure of glucose concentration is obtained in biological fluids.

In preferred embodiments, the portion of integration is selected so that the charge responsive to glucose concentration has predominantly the same algebraic sign throughout the portion, and so that the charge responsive to interfering components of the fluid (or to any specific interfering component) has a positive sign in one segment of the portion and a negative sign in another segment, so that the glucose-responsive charge, and thus sensitivity to glucose, is reinforced throughout the portion of integration, and the charge responsive to interfering substances at least partially cancels, thus reducing interference from those components or changes in concentration of those components. Total charge is normalized in the form of the ratio of total algebraic charge to total absolute value of charge; the lower limit of the voltage sweep is between −1.0 and −0.6 volts and the upper limit is between 0.7 and 1.1 volts; the voltage sweep includes dwell periods at the limits, and the rates of voltage change during the anodic and cathodic sweeps are constant; integration takes place continuously during one complete voltage sweep (or, alternatively, substantially including the anodic sweep between −0.45 volts and the upper limit, the dwell at the upper limit, and the entire cathodic sweep); the rate of voltage change during cathodic voltage sweep may be more rapid than during the anodic voltage sweep; and the voltage sweep may include holding periods between the limits at potentials at which glucose undergoes an electrochemical reaction.

According to another aspect of the invention, glucose concentration in biological fluids can be determined by measuring the current at the electrode at a point in a specific region between 0.2 volts and 0.6 volts during the anodic voltage variation selected to be sensitive to changes in levels of glucose concentration but relatively insensitive to levels of other constituents of the fluid.

DESCRIPTION OF THE PREFERRED EMBODIMENTS

We turn now to a description of the preferred embodiments of the invention, first briefly describing the drawings thereof.

INTEGRATION OF CURRENT

Figure 1:
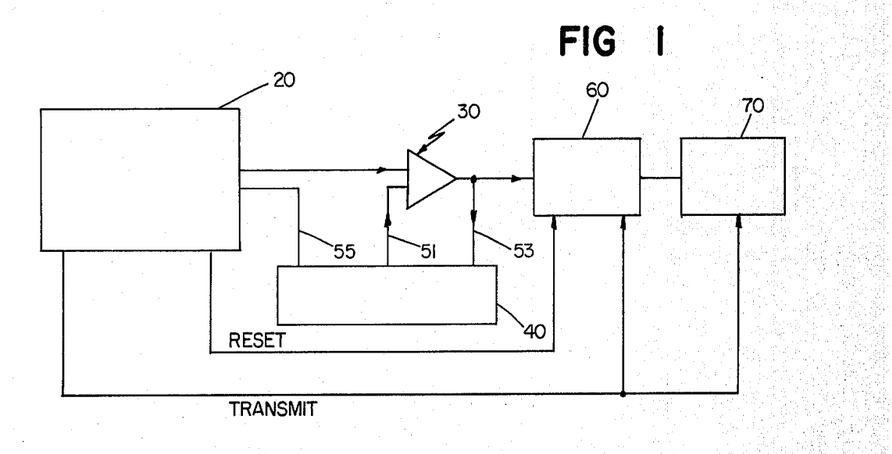
FIG. 1 is a block diagram of the circuitry for an implantable glucose sensor embodying one aspect of the invention.
Figure 3A:
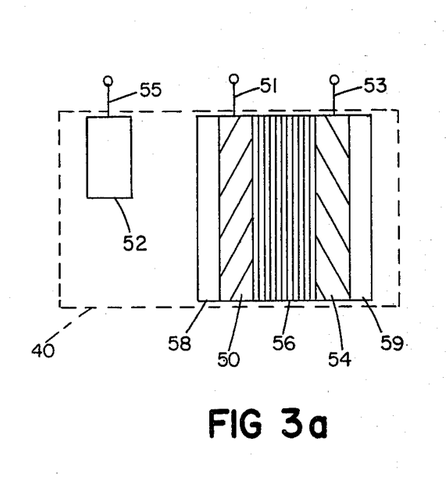
FIGS. 3a and 3b show, diagramatically, the elements of an electrode cell used with the embodiments of FIG. 1 or 2.
Figure 3B:
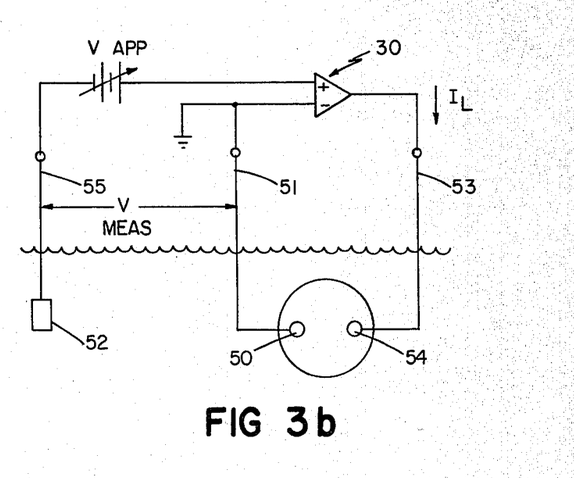

FIG. 1 shows in block form, one embodiment of implantable circuitry including glucose sensing cell 40. FIGS. 3a and 3b show potentiostat 30 connected to control the potential drop between glucose oxidation electrode 50 and reference electrode 52. Specifically, potentiostat 30 compares and equates that voltage (V meas.) to the voltage (V appl.) generated by function generator 20 by allowing current to flow in a measurement circuit formed by leads 51, glucose electrode 50, the biological medium, counter electrode 54, lead 53 and potentiostat 30. Reference electrode 52 is connected to the function generator by lead 55.

In FIG. 1, signal processor 60 is connected to the measurement circuit and integrates current in the circuit in response to timed signals from function generator 20. Modulator/transmitter 70 is connected to signal processor 60 and transmits an FM signal corresponding to the output of processor 60 in response to a transmit signal from function generator 20. Sensor cell 40 (FIG. 3) has a glucose oxidation electrode 50 separated by barrier 56

(which is an ion exchange membrane treated to allow passage of cations only) from counter electrode 54. A glucose-permeable membrane 58 separates electrode 50 from high molecular weight compounds in the biological medium, and a biocompatible hydrophobic membrane 59 at the counter electrode allows reaction products (gasses) to diffuse to surrounding tissue, while electrically insulating the electrode from that tissue. Reference electrode 52 is a silver/silver chloride electrode. Counter electrode 54 is a carbon electrode.

Glucose electrode 50 is a Teflon-bonded platinized platinum electrode prepared as follows: An electrode sheet is formed from a suspension of Teflon-30 (Dupont) and platinum black (Engelhard), respectively. This suspension is then filtered through a membrane to give a uniform layer of the Teflon and platinum on the membrane. This layered structure is then placed atop a platinum mesh screen with the Teflon-platinum layer mixture contacting the platinum screen. The resultant layered structure is subjected to pressure and then sintered to obtain the final electrode structure. The electrode is cut from the sheet.

Figure 4A:
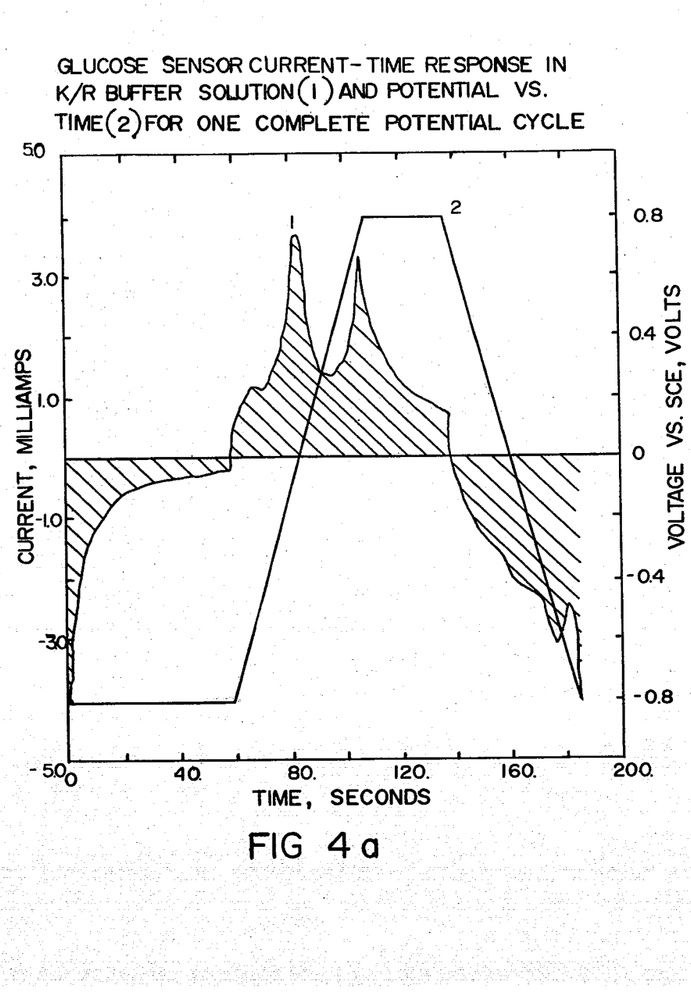
FIGS. 4a, b, c, d, e and f are graphs related to the embodiment of FIG. 1.

In operation, function generator 20 generates a waveform which varies back and forth between two limits. Line 2 in FIG. 4a shows a typical trapazoidal waveform in which voltage is maintained at $-0.8$ V for 60 sec., then increased at a rate of 2 volts/min. to $+0.8$ V. This region of increasing voltage is called the anodic voltage sweep. After a 30 second dwell at 0.8 V, voltage is decreased, again at 2 volts/min. to the lower limit of $-0.8$ V. The region of decreasing voltage is the cathodic voltage sweep. By selecting a voltage sweep which effectively permits glucose oxidation and rejuvenates the catalytic surface of the electrode, continuous sweeps and glucose concentration measurement are possible.

As the voltage is applied to the electrode, electrochemical reaction of glucose is catalyzed at electrode 50. Glucose from the surrounding tissue permeates the membrane, and reaction products are transported away from the electrode. Barrier 56 insulates the two electrodes, but allows transfer of cations to the counter electrode to complete the current measurement circuit.

The biological medium produces currents at specific portions of the voltage sweep. In particular glucose oxidation occurs at specific portions of the sweep; in those portions, the current generated (which will include current generated as a result of reaction of background constituents as well as glucose-responsive current) can be used to indicate glucose concentration. However, electrochemical reactions due to other fluid constituents—specifically urea and amino acids—may affect the current measurement and hinder determination of glucose concentration.

In certain portions of the sweep, the current related to a particular interfering substance is positive in one segment of the portion and negative in another segment, while the effect of glucose-related currents is essentially positive throughout the portion. By integrating cell current over time to obtain total charge at the electrode in that sweep portion, these glucose-reinforcing, interference-cancelling phenomena act to improve greatly the sensitivity to glucose concentration while at the same time reducing the interference experienced. Specifically, signal processor 60 integrates current and provides a measurement of total algebraic charge $Q_t$ over the region of integration; alternatively the signal process or can provide a signal representing ratio of the total algebraic charge to the absolute value of total charge $Q_t/|Q_t|$.

The graphs of FIG. 4 represent examples of operations conducted under simulated physiologic conditions. They are performed at 37° C. under an atmosphere of 95% nitrogen, 5% $CO_2$. The background fluid is a modified Kreb-Ringer buffer solution (0.109 M NaCl, 0.024 M $NaHCO_3$, 0.006 M $MgSO_4$, 0.001 M $NaH_2PO_4$, pH=7.4). Amino acids are provided in a stock solution of 23 dfferent amino acids at concentrations proportional to physiological concentrations. Urea is present in the physiological concentrations indicated. The potentiostat used (Princeton Applied Research Corp., Model PAR-173) has automatic IR compensation. The programmable functon generator is Model 73211 from Data Trak, Research, Inc. The glucose electrode has a geometric area of 0.19 $cm^2$, a Pt coat of 25 mg per $cm^2$ and a real area (from coulometric hydrogen stripping measurement) of 485 $cm^2$. The reference electrode is a standard saturated colomel (Hg, $Hg_2Cl_2$, KCl) electrode, and the glucose permeable membrane is Nucleopore, 500 Angstrom.

When the above-described voltage waveform (line 2 in FIG. 4a) is applied to the Krebs-Ringer buffer alone, the current at the electrode is first negative, then positive and finally negative, as indicated by line 1 in FIG. 4(a). The shaded area under line 1 represents charge, and the positive and negative areas essentially cancel.

Figure 4B:
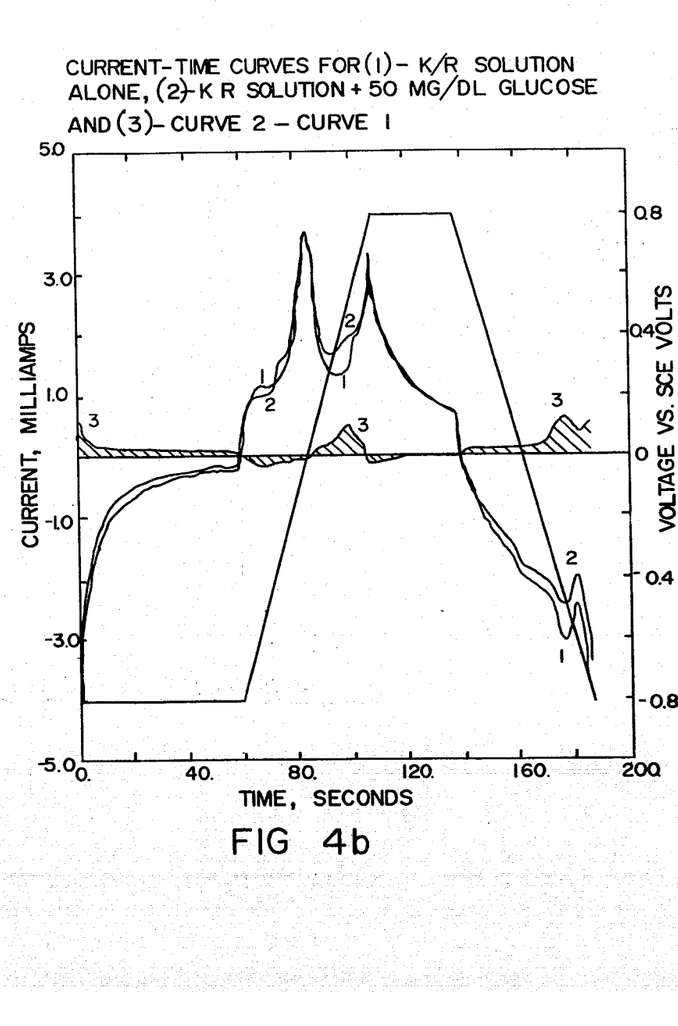

FIG. 4b shows current measured in the system before (line 1) and after (line 2) the addition of glucose. The difference attributable to glucose (line 3) results in a charge (shaded) which is essentially positive over the entire waveform.

With the addition of urea (FIG. 4c) or amino acids (FIG. 4d) to the system, the resulting current changes (line 2 in FIGS. 4c and d) are positive in some regions of the sweep and negative in other regions, while the current responsive to glucose (line 1) remains essentially positive throughout the sweep.

The following table shows that integrating current over the entire sweep provides an algebraic value of charge (Qt) (or a normalized value of charge in the form of the ratio of algebraic to total absolute charge $(Q_t/|Q_t|)$) which is sensitive to glucose concentration even in the presence of changing concentrations of amino acids and urea. FIGS. 4e and f specifically illustrate the above relationship in the presence of changing concentrations of amino acids.

| Glucose Electrode Response to Changes in Glucose and Amino Acid Concentration | | | | |
|---|---|---|---|---|
| Conc., mg/dl | | | | |
| Glucose | Amino Acids | Urea | $Q_t$, mCoul | $\dfrac{Q_t}{|Q_t|}$ |
| 50 | 35 | 40 | 20.0 | .087 |
| 63 | 35 | 40 | 22.6 | .099 |
| 75 | 35 | 40 | 24.5 | .107 |
| 88 | 35 | 40 | 26.0 | .114 |
| 100 | 35 | 40 | 27.6 | .122 |
| 113 | 35 | 40 | 28.0 | .123 |
| 125 | 35 | 40 | 30.0 | .132 |
| 160 | 35 | 40 | 31.9 | .141 |
| 175 | 35 | 40 | 33.7 | .148 |
| 200 | 35 | 40 | 36.3 | .160 |
| 250 | 35 | 40 | 41.0 | .180 |
| 50 | 50 | 40 | 23.8 | .109 |
| 63 | 50 | 40 | 24.3 | .111 |
| 75 | 50 | 40 | 24.9 | .114 |
| 88 | 50 | 40 | 27.3 | .126 |
| 100 | 50 | 40 | 28.8 | .133 |

-continued

Glucose Electrode Response to Changes in
Glucose and Amino Acid Concentration

| Conc., mg/dl | | | | |
|---|---|---|---|---|
| Glucose | Amino Acids | Urea | $Q_t$, mCoul | $\frac{Q_t}{|Q_t|}$ |
| 113 | 50 | 40 | 28.5 | .132 |
| 125 | 50 | 40 | 28.9 | .134 |
| 150 | 50 | 40 | 31.2 | .144 |
| 175 | 50 | 40 | 34.4 | .159 |
| 200 | 50 | 40 | 35.2 | .162 |
| 250 | 50 | 40 | 38.5 | .178 |
| 50 | 65 | 40 | 23.6 | .117 |
| 63 | 65 | 40 | 23.7 | .119 |
| 75 | 65 | 40 | 24.4 | .123 |
| 88 | 65 | 40 | 25.2 | .128 |
| 100 | 65 | 40 | 26.5 | .135 |
| 113 | 65 | 40 | 26.7 | .137 |
| 126 | 65 | 40 | 27.3 | .140 |
| 150 | 65 | 40 | 29.1 | .140 |
| 175 | 65 | 40 | 31.3 | .160 |
| 299 | 65 | 40 | 31.9 | .165 |
| 250 | 65 | 40 | 34.1 | .177 |

Thus, when integrating over the entire voltage sweep, the background charge (from the background solution and from the amino acids and urea) essentially cancels, while the glucose-responsive charge is essentially positive and, sensitivity to glucose is increased by integration. Moreover, changes in charges associated with changes in urea and amino acid concentrations, respectively, essentially cancel, thus enhancing sensitivity to glucose.

Figure 4C:
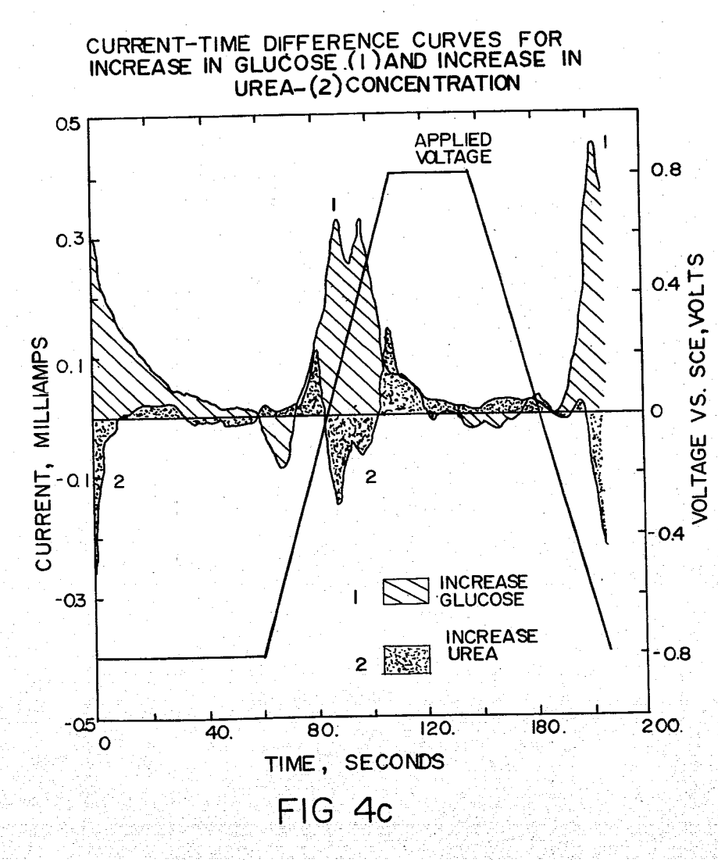
Figure 4D:
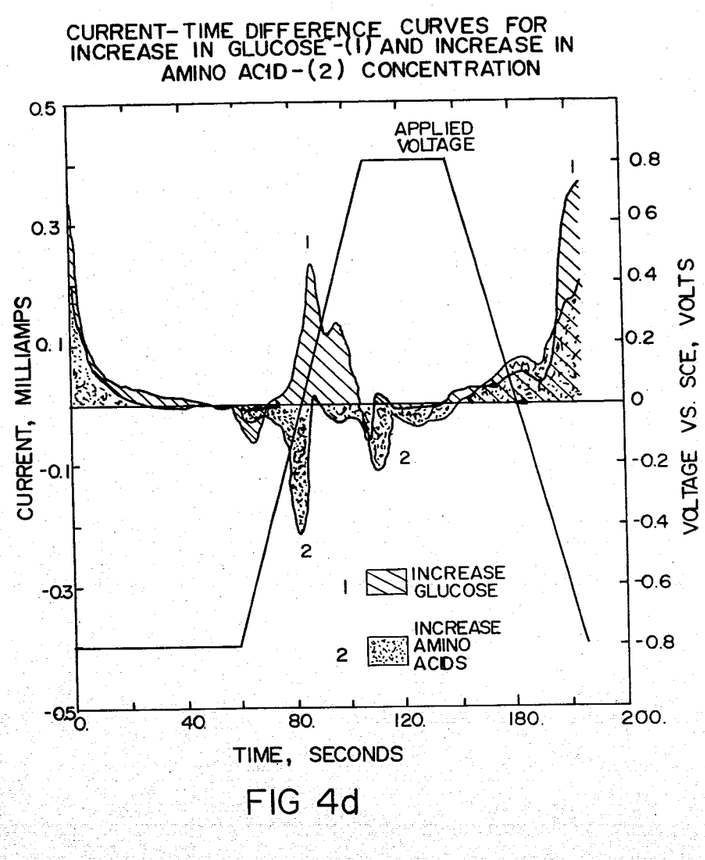
Figure 4E:
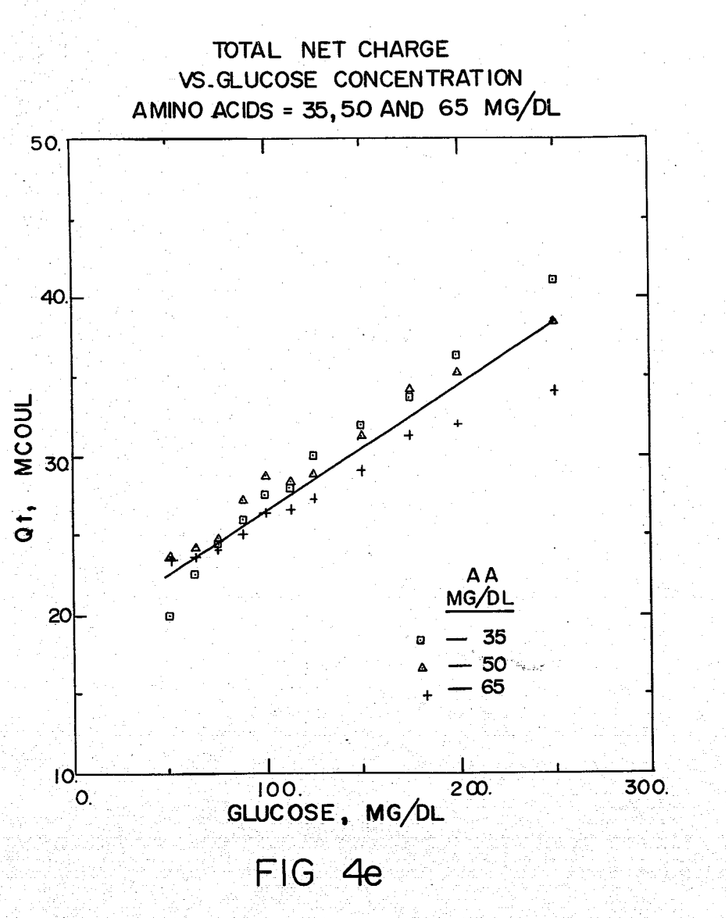
Figure 4F:
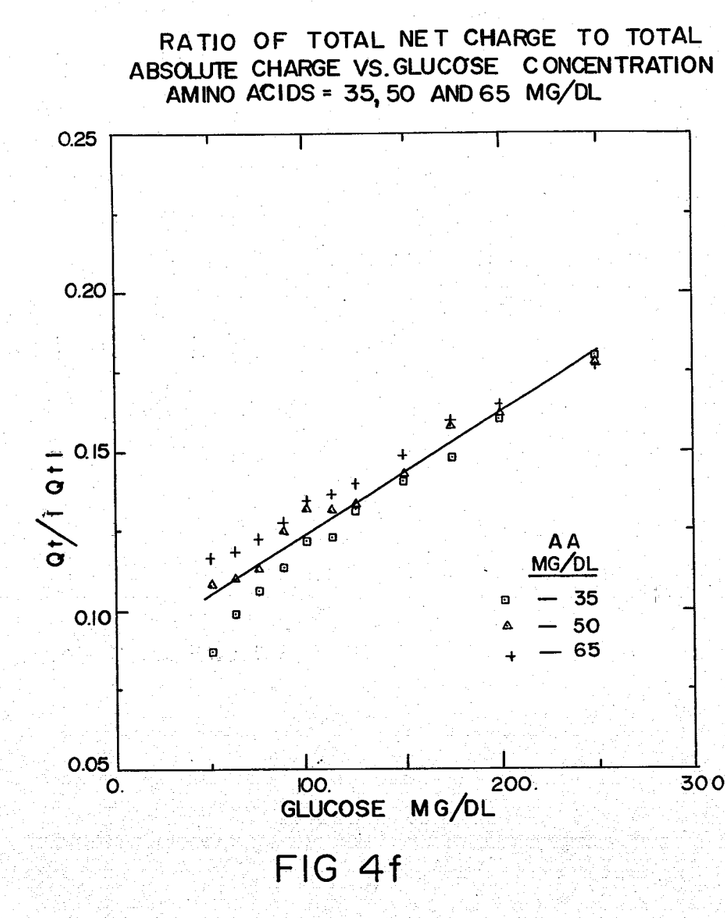

Referring specifically to FIGS. 4c and d, it is apparent that integration need not occur over the entire voltage sweep. Examination of a specific portion of the sweep—substantially including the portion of the anodic sweep from −0.45 volts to 0.8 volts, the dwell at the upper limit, and the entire cathodic sweep—also shows the requisite characteristics for selectivity and sensitivity.

Current Measurement

Figure 2:
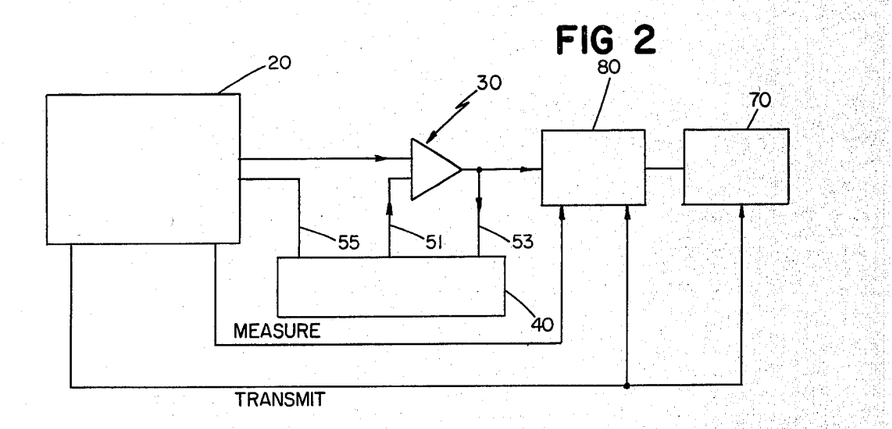
FIG. 2 is a block diagram of the circuitry for an implantable glucose sensor embodying another aspect of the invention.
Figure 5A:
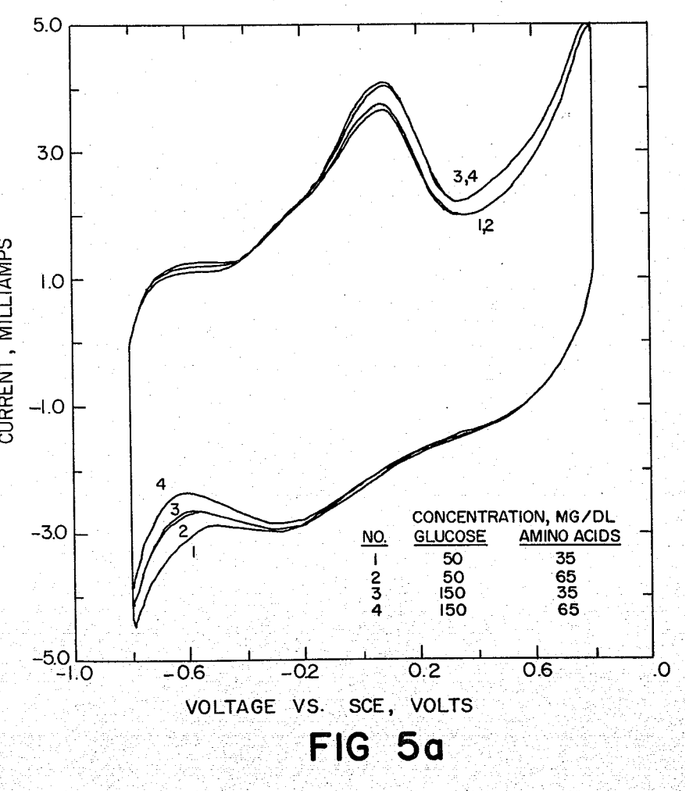
FIGS. 5a, b, and c are graphs related to the embodiment of FIG. 2.
Figure 5B:
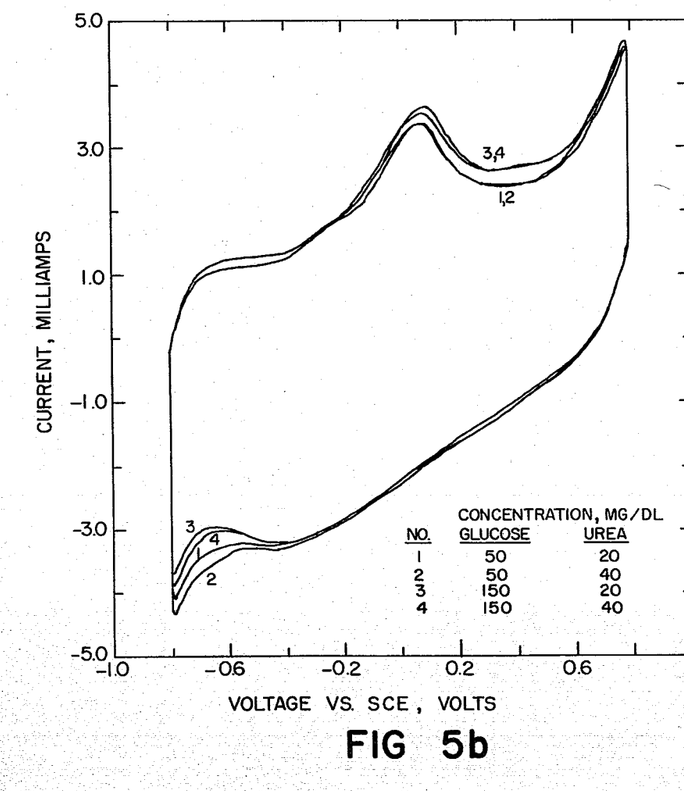
Figure 5C:
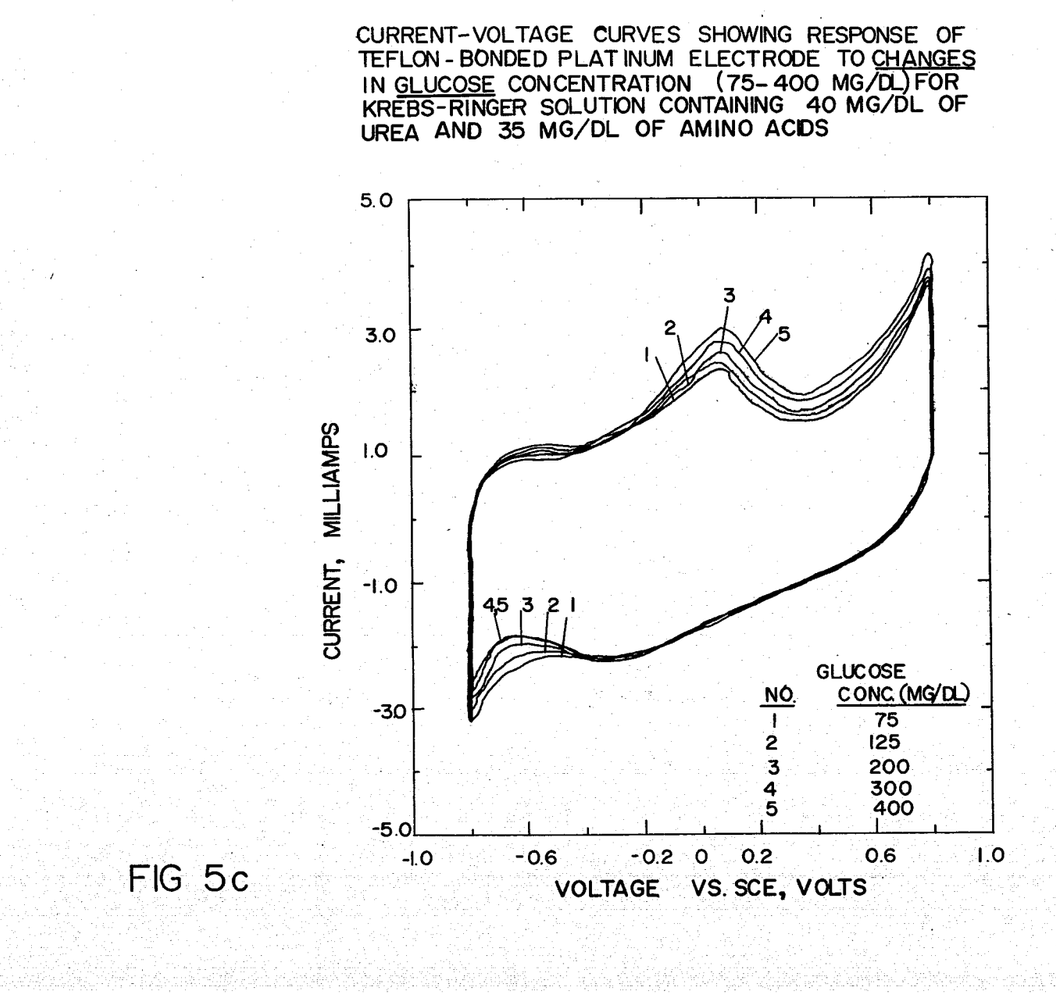

FIG. 2 shows a diagram of apparatus similar to FIG. 1, except that function generator 20 signals current measurement by current measurement means 80, and transmission of a signal representing that measurement by transmitter 70. FIGS. 5a, b and c represent the results of current measurement, under conditions described for the current integration examples above. The region between 0.2 and 0.6 volts of the anodic porton of the sweep shows a clear response to changes in glucose concentration, and a lack of response to changes in concentrations of amino acids and urea. Measurement at a point within that region (e.g., 0.3 volts) thus provides a measurement of glucose concentrations notwithstanding the presence of urea and amino acids. For example values of current at 0.3 V in the anodic scan for a Krebs-Ringer buffer containing 40 mg/dl of Urea and 35 mg/dl of amino acids, taken from a plot such as FIG. 5c, will show a linear relationship between current and glucose concentration.

The embodiments of both FIG. 1 and of FIG. 2 would include a receiver (not shown) outside of the organism in which the sensor is implanted, to recieve the signal transmitted by the sensor and translate that signal into data representing glucose concentration. Alternatively the receiver could trigger an alarm when glucose concentration varies outside predetermined limits.

Other Embodiments

Other embodiments are within the scope of the following claims. By way of example only, the voltage waveform may be varied in several ways: the dwell times can be changed but should preferably be at least 2 seconds; the lower limit can be increased to, e.g., −1.0 volts, but excessive generation of hydrogen results from a limit significantly below that level. The upper limit can vary, e.g., from 0.7 to 1.1 volts; a voltage significantly above 1.1 V causes corrosion of the electrode. Holding periods may be introduced during the anodic and/or the cathodic portion of the sweep, preferably at potentials at which glucose reactions occur so as to increase the amount of time spent at such potentials and enhance sensitivity and selectivity to glucose; the rate of voltage change in the anodic and cathodic sweeps may be different—e.g., the anodic sweep may be relative slower to increase the amount of time spent at voltages which produce currents sensitive and selective for glucose. With respect to the current measurement embodiment of FIG. 2, the voltage variation could include discontinuities such as jumps from a limit to the measuring voltage.

The claims include glucose sensors that are not implanted—e.g., clinical laboratory sensors. The biological fluids can include any fluids taken from living organisms or fluids simulating conditions in a living organism including, without limitation, blood, urine, buffer solutions, and saline solutions.

We claim:

1. Apparatus implantable in a living body for sensing the concentration of glucose in biological fluids, comprising
    an electrode for catalytically promoting electrochemical oxidation of glucose,
    a voltage source,
    means for applying a varying voltage from said source to said electrode to cause a current flow therethrough,
    means for integrating current at the electrode with respect to time, and
    control means automatically operative without manual intervention to cause said voltage to sweep over a range in a first direction from a first limit to a second limit and in the reverse direction back toward said first limit, and to selectively activate said means for integrating during a period including at least a portion of said voltage sweep in both directions selected to produce a total charge sensitive to glucose concentration and relatively insensitive to other components in the fluid.

2. The apparatus of claim 1 in which said portion is selected so that the charge responsive to glucose concentration has predominantly the same algebraic sign throughout said period, and so that the charge responsive to interfering components of said fluid has a positive sign in one segment of said period and a negative sign in another segment of said period, whereby the glucose-responsive charge, and thus sensitivity to glucose, is reinforced, and the charge responsive to interfering substances at least partially cancels, thus reducing such interference.

3. The apparatus of claim 1 or 2 in which the lower limit of such voltage sweep is between −1.0 and −0.6 volts and the upper limit is between 0.7 and 1.1 volts, said sweep including an anodic sweep from said lower to said upper limit and a cathodic sweep from said upper to said lower limit.

4. The apparatus of claim 1 or 2 in which said voltage sweep includes dwell periods at said upper and lower limits, and the rate of voltage change during said anodic and cathodic sweeps is constant.

5. The apparatus of claim 1 or 2 in which said integration takes place continuously during one complete voltage sweep.

6. The apparatus of claim 1 or 2 in which said period includes the anodic sweep between −0.45 volts and said upper limit, the dwell at said upper limit, and the entire cathodic voltage sweep.

7. The apparatus of claim 1 or 2 in which the rate of voltage change during said cathodic voltage sweep is more rapid than during said anodic voltage sweep.

8. The apparatus of claim 1 or 2 in which said varying of said applied voltage ceases during holding periods between said limits, said holding periods being at potentials at which glucose undergoes an electrochemical reaction.

9. The apparatus of claim 1 or 2 in which said period is selected so that the charge attributable to any specific interfering component of the fluid cancels, whereby changes in concentration of that specific component do not affect the charge measured.

10. The apparatus of claim 1 or 2 in which said apparatus includes normalizing means for forming the ratio of said total charge to the total absolute value of charge during said period.

11. Apparatus according to claim 10 wherein said voltage variation includes an anodic sweep and a cathodic sweep, said rate of voltage variation being between 0.5 volts/min and 4 volts/min.

12. Apparatus according to claim 11 in which the rate of voltage change during said cathodic sweep is more rapid than during said anodic sweep.

13. Apparatus for sensing the concentration of glucose in biological fluids comprising
an electrode for catalytically promoting electrochemical oxidation of glucose,
a voltage source,
means for applying a varying voltage from the source to said electrode to cause a current to flow therethrough,
means for measuring current at said electrode, and
control means automatically operative without manual intervention to cause said voltage to sweep over a range in a first direction from a first limit to a second limit and in the reverse direction back toward said first limit, and to selectively activate said means for measuring at at least one isolated point, between 0.2 volts and 0.6 volts during the anodic variation of the voltage sweep, selected to be sensitive to changes in levels of glucose concentration in said fluid but relatively insensitive to levels of other constituents of said fluid.

14. Apparatus of claim 13 in which said lower limit of said voltage variation is between −1.0 and −0.6 volts and the said upper limit is between 0.7 and 1.1 volts.

15. Apparatus of claim 13 in which the rate of change of said voltage variation is constant between said limits, and includes dwell periods at each limit.

16. Apparatus according to claim 15 in which said dwell periods are greater than 2 seconds.

* * * * *